United States Patent [19]

Czernecki et al.

[11] Patent Number: 5,075,336

[45] Date of Patent: Dec. 24, 1991

[54] ALKALINE EARTH METAL SALTS OF OXA POLYACID COMPOUNDS

[75] Inventors: Stanislas Czernecki, Rubelles - Maincy; Claude Fugier, Le Havre; Yannis Tsouderos, La Celle St Cloud, all of France

[73] Assignee: Adir et Compagnie, Courbevoie, France

[21] Appl. No.: 657,140

[22] Filed: Feb. 15, 1991

[30] Foreign Application Priority Data

Feb. 27, 1990 [FR] France .................. 90 02392

[51] Int. Cl.⁵ .............................................. A61K 31/19
[52] U.S. Cl. ....................... 514/574; 562/582; 562/583
[58] Field of Search ................. 562/582, 583; 514/574

[56] References Cited

U.S. PATENT DOCUMENTS 4,025,450  5/1977  Lamberti et al. .................. 562/583
4,260,513  4/1981  Lamberti et al. .................. 562/583

FOREIGN PATENT DOCUMENTS 592604  9/1947  United Kingdom ................ 562/583

*Primary Examiner*—Bruce Gray
*Attorney, Agent, or Firm*—Gordon W. Hueschen

[57] ABSTRACT

Compounds of general formula

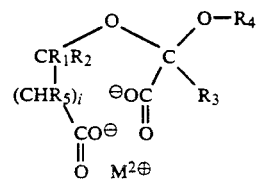

in which:
M is an alkaline earth metal,
$R_1$, $R_2$, $R_3$, $R_4$, $R_5$ and i being defined in the description.

Medicaments.

8 Claims, No Drawings

ALKALINE EARTH METAL SALTS OF OXA POLYACID COMPOUNDS

The present invention relates to new alkaline earth metal salts of oxa polyacid compounds, process for preparing them and pharmaceutical compositions containing them.

The supply of divalent cations is indispensable to the life of animal organisms, in particular of mammals and thus of man. This supply is generally ensured by the food.

However, when the metabolisms of the organism are in disequilibrium, it is essential to supply a supplement of divalent cations so as to treat diseases such as: oligoelement deficiencies, magnesium deficiencies and osteoporosis.

Some publications in the literature, such as, for example:
Gastineau, Poc. Straff. Meeting Mayo Clinic 35 105–111 (1960)
Skoryna, Can. Med. Assoc. 125 (7), 702–712 (1981)
Skoryna, Trace Subst. Environ. Health 18, 3–23 (1984)
speak of the activity of strontium lactate, gluconate and carbonate in the treatment of osteoporosis.

The Applicant has now discovered new divalent cation salts of oxa polyacid compounds, the bioavailability of which is distinctly improved compared with all the other known salts.

Some of them, and in particular the strontium, calcium and magnesium salts, have a surprising activity on the osseous metabolism, that is to say they strongly activate osseous formation while, in parallel, inhibiting osseous resorption.

Some alkali metal salts of oxa polyacid compounds have already been described in the literature (DE 22 48 708 B2) with regard to their detergent properties, without any biological property having been demonstrated.

More specifically, the invention relates to the alkaline earth metal salts of general formula (I):

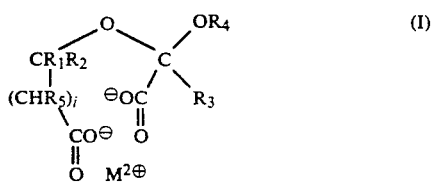

in which
$R_1$, $R_2$, $R_3$ and $R_5$ each represent, independently of one another, a hydrogen atom, a straight-chain or branched lower alkyl group having 1 to 4 carbon atoms or a hydroxyl, hydroxyalkyl, alkoxy, alkoxyalkyl or carboxyalkyl group,
i may take the values 0 and 1,
$R_4$ is a hydrogen atom, a straight-chain or branched lower alkyl group having 1 to 4 carbon atoms, an optionally substituted aryl or arylakyl group or a carboxyalkyl group, with the proviso that when $R_1=R_3=H$, $R_2=CH_2OH$ and i=0 and when $R_1=R_2=R_3=H$ and I=0, $R_4$ is then other than $CH_3$, it being understood that the substituted term with the expressions aryl or arylalkyl indicates that the aromatic rings may be substituted by one or more alkyl, nitro, alkoxy, hydroxyl, halogen or trifluoromethyl groups, M represents an alkaline earth metal,
their isomers, epimers, diastereoisomers and enantiomers, which may be isolated or in the form of a mixture.

Amongst the compounds of the invention, the strontium salts of general formula (I) are currently preferred.

The invention also extends to the process for obtaining the compounds of general formula (I), which comprises reacting a compound of formula (II):

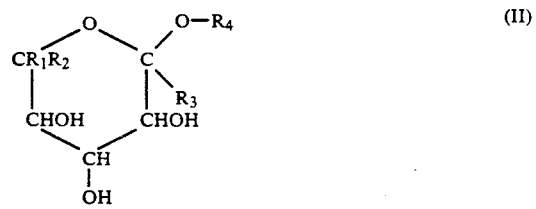

in which $R_1$, $R_2$, $R_3$ and $R_4$ have the same meaning as in formula (I), with periodic acid so as to obtain a compound of general formula (III):

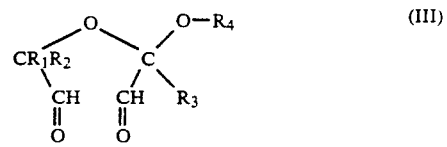

in which $R_1$, $R_2$, $R_3$ and $R_4$ have the same meaning as in formula (I), which is subjected, in solution in a alcohol XOH to an oxidation reaction with bromine so as to obtain the polyester compound of general formula (IV):

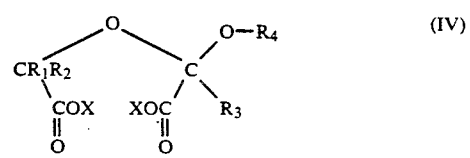

in which $R_1$, $R_2$, $R_3$ and $R_4$ have the same meaning as in formula (I) and X is a straight-chain or branched lower alkyl radical having 1 to 4 carbon atoms, which is subjected to a saponification reaction in an aqueous-alcoholic medium with an alkaline earth metal hydroxide so as to obtain the corresponding alkaline earth metal salt of general formula (IA):

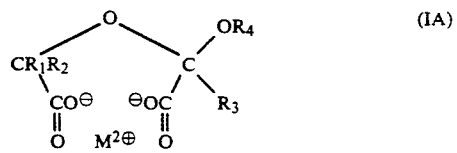

in which $R_1$, $R_2$, $R_3$, $R_4$ and M have the same meaning as in formula (I).

The corresponding acid compounds may be obtained by acidification with hydrochloric acid.

The compounds of formula (I) for which i=1 are particular cases of the present invention.

These compounds are prepared from an alkyl 4,6-O-benzylidene glucopyrannoside of general formula (V):

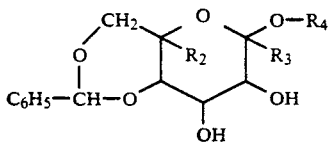

in which $R_2$, $R_3$ and $R_4$ have the same meaning as in formula (I), which is reacted with periodic acid to obtain the dialdehyde, which is then deprotected in order to obtain the compound of general formula (VI):

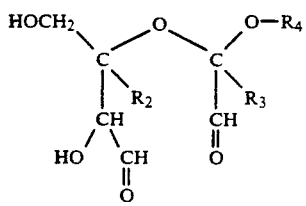

in which $R_2$, $R_3$ and $R_4$ have the same meaning as in formula (I), which is subjected, in solution in an alcohol XOH, to an oxidation reaction with bromine so as to obtain the polyester compound of general formula (VII)

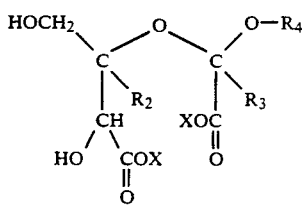

in which $R_2$, $R_3$ and $R_4$ have the same meaning as in formula (I) and X is a straight-chain or branched lower alkyl radical having 1 to 4 carbon atoms, which is subjected to a saponification reaction in an aqueous-alcoholic medium with an alkaline earth metal hydroxide so as to obtain the corresponding alkaline earth metal salt of general formula (IB)

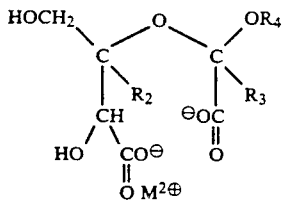

in which $R_2$, $R_3$, $R_4$ and M have the same meaning as in formula (I).

The alkaline earth metal salts of general formula (I) have, on the one hand, an excellent bioavailability and, on the other hand, a remarkable activity, strongly stimulating osseous formation while, in parallel, inhibiting osseous resorption. These particularly valuable properties permit their use in the treatment of some osseous diseases, in particular those resulting from mineralization disorders, such as osteoporosis or tumors involving osseous metastases. They may also be used in the treatment of cutaneous and vascular aging, liver complaints and dental complaints. The calcium and magnesium salts may be used in the treatment of some complaints, such as deficiencies, which require a therapeutic supply of divalent cations.

The present invention also relates to the pharmaceutical compositions containing, as active principle, one of the salts of general formula (I) mixed or combined with an inert, non-toxic and pharmaceutically appropriate excipient such as, for example, distilled water, glucose, lactose, starch, talc, ethyl cellulose, magnesium stearate, colloidal silica or cacao butter.

The pharmaceutical compositions thus obtained are generally in dose form and, depending on the complaints treated and on the age and the sex of the patient, may contain from 1 to 1000 mg of active principle.

They may take the form of tablets, coated tablets, capsules, injectable or drinkable solutions or suppositories and, depending on the case, may be administered orally, rectally or parenterally in a dose of 1 to 1000 mg once to several times per day.

The following examples illustrate the invention and do not limit it in any way.

EXAMPLE 1

Strontium 2-ethoxy-4-hydroxymethyl-3-oxa pentanedioate (compound (I) with i=0, $R_1=CH_2OH$, $R_2=R_3=H$, $R_4=C_2H_5$, $M^{2+}=Sr^{2+}$ obtained from ethyl β-D-glucopyrannoside)

Stage I: Ethyl 2,3,4,6-tetra-O-acetyl-β-D-glucopyrannoside 1 liter of toluene and 23.8 g (0.517 mol) of anhydrous ethanol are charged into a reactor under a nitrogen atmosphere. A previously prepared solution of 200 g (0.513 mol) of β-D-glucose pentaacetate in 2 liters of toluene is then added at ambient temperature. The mixture is heated to 40° C. and a previously prepared solution of 30 cm³ (0.258 mol) of tin tetrachloride in 1 liter of toluene is then added in the course of about 10 minutes. The mixture is then kept at 40° C. for 55 minutes, hydrolyzed with water, dried over magnesium sulfate and then concentrated under reduced pressure.

The crude product obtained is taken up in 300 cm³ of an ethanol/water mixture (50/50), with vigorous stirring. The suspension is cooled to −10° C. and then filtered under argon.

The moist solid is dissolved hot (≃60° C.) in 800 cm³ of an ethanol/water mixture (60/40). The solution is cooled to −10° C. and the product is allowed to crystallize for 1 hour and is then filtered off under argon. The product is dried under vacuum in the presence of $P_2O_5$ to constant weight.

79 g (41%) of ethyl 2,3,4,6-tetra-O-acetyl-β-D-glucopyrannoside are thus obtained int he form of a fine white powder.

Melting point: 106° C.

Stage II: Ethyl β-D-glucopyrannoside 67.68 g of ethyl 2,3,4,6-tetra-O-acetyl-β-D-glucopyrannoside and 382 cm³ of anhydrous methanol are charged into a reactor under a nitrogen atmosphere. The suspension is stirred at ambient temperature and then run, in the course of 5 minutes, into 18 cm³ (0.018 mol) of a molar solution of sodium methylate in methanol.

The mixture is stirred for 110 minutes at 23°–24° C. and then neutralized by the addition of 21.5 g of Amberlite H+ resin. The resins are removed by filtering off and the reaction mixture is then brought to dryness under reduced pressure.

36.5 g (100%) of ethyl β-D-flucopyrannoside are thus obtained in the form of a deliquescent yellow mass.

Stage III: 2-ethoxy-4-hydroxymethyl-3-oxa glutaraldehyde 35 g of ethyl β-D-glucopyrannoside and 424 cm³ of water are charged into a reactor under an atmosphere of nitrogen. The mixture is stirred vigorously and a previously prepared solution of 8.2 g (0.356 mol) of periodic acid in 900 cm³ of water is run in rapidly at ambient temperature. The reaction mixture is stirred for 3 hours at ambient temperature, then cooled and neutralized by addition of 64 cm³ of 10N sodium hydroxide solution. The water is removed by distillation under reduced pressure.

The white solid obtained is taken up in 828 cm³ of ethanol and stirred vigorously for 1 hour. The insoluble matter is removed by filtration and the ethanolic filtrate is concentrated at 40° C. under reduced pressure.

30.1 g (90.4%) of 2l-ethoxy-4-hydroxymethyl-3-oxa glutaraldehyde are thus obtained.

Stage IV: Methyl 2-ethoxy-4-hydroxymethyl-3-oxa pentanedioate.

43.4 g of 2-ethoxy-4-hydroxymethyl-3-oxa glutaraldehyde, 220.5 g of sodium bicarbonate and 221 cm³ of a methanol/water mixture (90/10) are charged into a reactor under an atmosphere of nitrogen. The mixture is stirred at ambient temperature and a previously prepared solution of 148 g of bromine in 773 cm³ of a methanol/water mixture (90/10) is run in the course of 2 hours. The reaction mixture is then stirred for 2 hours at ambient temperature and 33.75 g of sodium thiosulfate are then introduced in several portions.

The suspension obtained is filtered, 280 cm³ of water are added to the filtrate and the methanol is removed at 40° C. under reduced pressure. The concentrate is extracted with 3 times 550 cm³ of methylene chloride and the extract phases are washed with 226 cm³ of water and then dried over magnesium sulfate and brought to dryness under reduced pressure.

25.5 g (69.8%) of methyl 2-ethoxy-4-hydroxymethyl-3-oxa pentanedioate are thus obtained in the form of a yellow syrupy compound.

NMR 200 MHz (DCDl₃, TMS)

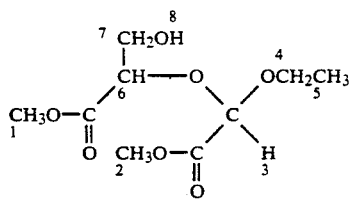

1.1 ppm triplet $CH_3$ 5; 3.2 ppm multiplet $CH_6$; 3.6 ppm multiplet $CH_2$ 4; 3.6 to 3.7 ppm singlets 2$CH_3$ 1 and 2; 3.8 ppm multiplet $CH_2$ 7; 4.3 ppm singlet CH 3; 5 ppm singlet OH 8

Microanalysis:
Calculated: C 45.76; H 6.82.
Found: C 45.80; H 6.86.

Stage V: Strontium 2-ethoxy-4-hydroxymethyl-3-oxa pentanedioate (obtained using ethyl β-D-glucopyrannoside)

10.53 g of strontium hydroxide in 120 cm³ of water are charged into a reactor under an atmosphere of nitrogen. The mixture is refluxed for 15 minutes and the insoluble matter is removed by filtering hot. A previously prepared solution of 9.45 g of methyl 2-ethoxy-4-hydroxymethyl-3-oxa pentanedioate in 20 cm³ of methanol is then added to the filtrate. The reaction mixture is refluxed for 1 hour, cooled to 30° C., concentrated under reduced pressure to two thirds of the initial volume and then chilled at 0° C. until crystallization of the product is complete. The strontium salt is isolated by filtering off and then dried under vacuum at 30° C. in the presence of $P_2O_5$.

6.36 g (65%) of strontium 2-ethoxy-4-hydroxymethyl-3-oxa pentanedioate are thus obtained in the form of a white powder.

Melting point higher than 260° C.
NMR 200 MHz (D₂O, TMS)

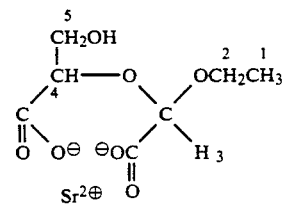

1.10 ppm triplet $CH_3$; 3.60–3.45 ppm multiplet $CH_2$ 2; 3.81 ppm multiplet $CH_2$ 5; 4.15 ppm multiplet CH 4; 4.80 ppm singlet CH 3.

Microanalysis:
Calculated: C 28.42; H 4.09.
Found: C 28.45; H 4.13.
Specific optical rotation:
$[\alpha]_D^{20} = +42$ (C=5 mg in 1 ml of water)

Example 2:

Strontium 2-propoxy-4-hydroxymethyl-3-oxa pentanedioate (Compound (I) with i=0, $R_1$=$CH_2OH$, $R_2$=$R_3$=H, $R_4$=$CH_2CH_2CH_3$, $M_{2+}$=$Sr^{2+}$ obtained using propyl β-D-glucopyrannoside as starting material)

The procedure is carried out in the same way as for Example 1, replacing anhydrous ethanol by anhydrous n-propanol in stage I.

Melting point higher than 260° C.
NMR 200 MHz (CD₃OD, TMS)

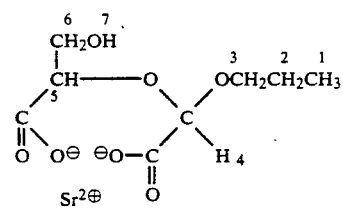

0.90 ppm multiplet $CH_3$ 1; 1.6 ppm multiplet $CH_2$ 2; 3.63 ppm multiplet $CH_2$ ; 3.95 ppm multiplet $CH_2$ 3; 4.45 ppm multiplet CH 5; 5.17 ppm singlet CH 4; 5.35 ppm singlet OH 7.

EXAMPLE 3

Strontium 2-ethoxy-4-hydroxymethyl-3-oxa pentanedioate (Compound (I) with i=0, $R_1$=$CH_2OH$, $R_2$=$R_3$=H, $R_4$=$C_2H_5$, $M^{2+}$=$Sr^{2+}$ obtained using ethyl α-D-mannopyrannoside as the starting material)

Stage I: Ethyl α-D-mannopyrannoside 100 cm³ of absolute ethanol, 12 g of Amberlite H⁺ resin and 18.02 g (0.100 mol) of D-(+)-mannose are charged into a reactor under an atmosphere of nitrogen.

The reaction mixture is refluxed for 7 hours and then cooled and the resin is removed by filtering off.

After rinsing the resin with absolute ethanol, the filtrates are combined and concentrated under reduced pressure.

After bringing to dryness, 20.9 g (100%) of ethyl α-D-mannopyrannoside are obtained.

Stage II: 2-ethoxy-4-hydroxymethyl-3-oxa glutaraldehyde 20 g of ethyl α-D-mannopyrannoside and 242 cm³ of water are charged into a reactor under an atmosphere of nitrogen. The mixture is stirred vigorously and a previously prepared solution of 46.4 g (0.204 mol) of periodic acid in 514 cm³ of water is run in rapidly at ambient temperature. The reaction mixture is stirred for 3 hours at ambient temperature, then cooled, neutralized by the addition of 36.6 cm³ of 10N sodium hydroxide solution and brought to dryness by distillation under reduced pressure.

The residue is taken up in 473 cm³ of ethanol and the mixture is stirred vigorously for 1 hour. The insoluble matter is removed by filtering off and the ethanolic filtrate is concentrated at 40° C. under reduced pressure.

16.8 g (88.3% of 2-ethoxy-4-hydroxymethyl-3-oxa glutaraldehyde are obtained.

Stage III: Methyl 2-ethoxy-4-hydroxymethyl-3-oxa pentanedioate 0.7 g of 2-ethoxy-4-hydroxymethyl-3-oxa glutaraldehyde, 6 g of sodium bicarbonate and 10 cm³ of a methanol/water mixture (90/10) are charged into a round-bottomed flask under an atmospheres of nitrogen. The mixture is stirred for 10 minutes at ambient temperature and a previously prepared solution of 3.2 g of bromine in 10 cm³ of a methanol/water mixture (90/10) is then added dropwise.

The reaction mixture is then stirred for 4 hours at temperature and 0.55 g of sodium thiosulfate is then added.

The suspension is filtered, 4.5 cm³ of water are added to the filtrate and the methanol is removed at 40° C. under reduced pressure. The concentrate is extracted with 3 times 35 cm³ of methylene chloride and the organic phases are washed with 10 cm³ of water and then dried over magnesium sulfate and brought to dryness under reduced pressure.

0.75 g (100%) of methyl 2-ethoxy-4-hydroxymethyl-3-oxa pentanedioate is obtained.

Microanalysis:
Calculated C 45.76; H 6.82.
Found C 45.8; H 6.9.

Stage IV: Strontium 2-ethoxy-4-hydroxymethyl-3-oxa pentanedioate (obtained using ethyl α-D-mannopyrannoside as the starting material)

0.89 g of strontium hydroxide in 20 cm³ of water is charged into a round-bottomed flask under an atmosphere of nitrogen. The mixture is refluxed for 15 minutes and the insoluble matter is then removed by filtering hot. A previously prepared solution of 0.8 g of methyl 2-ethoxy-4-hydroxymethyl-3-oxa pentanedioate in 2 cm³ of methanol is then added to the filtrate. The reaction mixture is refluxed for 1 hour and then brought to dryness by evaporation under reduced pressure.

The residue resulting from bringing to dryness is redissolved hot in 20 cm³ of water and the solution is filtered hot before being brought to dryness again. The residue obtained is dried under vacuum at 120° C. for 5 hours.

0.7 g (74%) of strontium 2-ethoxy-4-hydroxy-methyl-3-oxa pentanedioate is thus obtained in the form of a white powder.

NMR 200 MHz (D₂O, TMS)

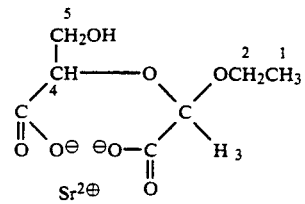

1.10 ppm triplet CH₃ 1; 3.60–3.47 ppm multiplet CH₂ 2; 3.92–3.77 ppm multiplet CH₂ 5; 4.20 ppm doublet dedoubled CH 4; 5.00 ppm singlet CH 3:

Specific optical rotation:
$[\alpha]_D^{20} = +44$ (C=5 mg in 1 ml of water)

EXAMPLE 4

Magnesium 2-ethoxy-4-hydroxymethyl-3-oxa pentanedioate (compound (I) with i=0, $R_1=CH_2OH$, $R_2=R_3=H$, $R_4=C_2H_5$, $M^{2+}=Mg^{2+}$ obtained using ethyl β-D-glucopyrannoside as the starting material)

The procedure is carried out in the same way as for Example 1, replacing strontium hydroxide by magnesium hydroxide in stage V.

EXAMPLE 5

Calcium 2-ethoxy-4-hydroxymethyl-3-oxa pentanedioate (compound (I) with i=0, $R_1=CH_2OH$, $R_2=R_3=H$, $R_4=C_2H_5$, $M^{2+}=Ca^{2+}$ obtained using ethyl β-D-glucopyrannoside as the starting material)

The procedure is carried out in the same way as for Example 1, replacing strontium hydroxide by calcium hydroxide in stage V.

EXAMPLE 6

Tablet containing 500 mg of strontium 2-ethoxy-4-hydroxymethyl-3-oxa pentanedioate obtained using ethyl β-D-glucopyrannoside as the starting material

| Formulation for 10000 tablets | |
| --- | --- |
| Strontium 2-ethoxy-4-hydroxymethyl-3-oxa pentanedioate | 5 kg |
| Lactose | 2.150 kg |
| Magnesium stearate | 0.05 kg |
| Colloidal silica | 0.005 kg |
| Maize starch | 0.595 kg |

EXAMPLE 7 capsule containing 5 mg of strontium 2-ethoxy-4-hydroxymethyl-3-oxa pentanedioate obtained using ethyl β-D-glucopyrannoside as the starting material

| Formulation for 1000 capsules | |
| --- | --- |
| Strontium 2-ethoxy-4-hydroxymethyl-3-oxa pentanedioate | 5 g |
| Lactose | 15 g |
| Maize starch | 25 g |
| Talc | 5 g |

EXAMPLE 8 pharmacological study: activity on osseous formation and osseous resorption a) principle Osteoblast and osteoclast have between them communication systems which are poorly known and which explain the synchronism of their activities permitting osseous replenishment.

It can be considered that these communication systems are preserved in bones kept in tissue culture and that it is thus possible to assess the activity of physiological or therapeutic molecules in vitro on osseous cells under conditions close to physiological conditions.

The activity on osseous formation and the antiresorbing activity of compounds potentially active as medicaments may be detected and measured in vitro in tissue culture.

b) Methodology

α) Osseous formation

Demi-calvarias of newly born mice (1-2 days) are cultured on gratings in BGJ medium containing tritiated proline. The explants are cultured for 48 h in the presence of the tested compound at 37° C. and at the end of the culture the bones are washed in trichloroacetic acid containing non-radioactive proline in order to remove the $^3$H-proline which has not been incorporated.

After washing and dissolving in sodium hydroxide solution, the incorporation of the labler in the bone and the amount of total proteins are counted. The effect of the product on the incorporation of proline in the bone in culture is thus evaluated.

Each treated demi-calvaria is compared with the untreated demi-calvaria which serves as control and the T/C ratio is calculated.

$$T/C = \frac{\text{osseous formation in the presence of the product tested}}{\text{osseous formation in the control}}$$

A stimulation of the osseous formation is reflected by a higher incorporation of tritiated proline in the treated demi-calvaria than in the control (T/C>1). An inhibition of the osseous formation is shown by a T/C ratio of <1.

The compounds were tested at concentrations of $10^{-4}$, $10^{-6}$, $10^{-8}$, $10^{-10}$ and $10^{-12}$M.

6 to 9 experiments were carried out per point.

β) osseous resorption 18-day pregnant rats are injected with 150 μcuries of $^{45}$Ca subcutaneously.

On the 19th day the rats are sacrificed and the foetuses are removed, immersed in a bath of alcohol at 70° are then two baths of PBS and killed by cutting off the head. The two forearms are dissected, the skin, the tendons and the muscles are removed and the cartilaginous extremities are cut off. The forearms are cultured in 24-well culture boxes in the presence of 1.5 ml of MEM for 24 hours for equilibration. At the end of said 24 hours, the medium is replaced by 1.5 ml of BGJB supplemented with 10% of foetal calf serum. The resorption is stimulated in all of the samples by 400 mg of PTH. The bones are cultured for two successive periods of 72 hours each and the culture media are removed to determine the amount of $^{45}$Ca salted out at the end of each of these two periods. At the end of the second period (7 days after the start of culture), the bones are immersed for 24 hours in 1.5 ml of 10% formic acid and the $^{45}$Ca salted out from the bones is also determined in a scintillation counter.

The results are expressed for each of the two culture periods by the treated/control ratio calculated in the following way:

$$\frac{\left[\frac{\text{radioactivity of the medium}}{\text{radioactivity salted out from the bone}}\right]_{\text{treated}}}{\left[\frac{\text{radioactivity of the medium}}{\text{radioactivity salted out from the bone}}\right]_{\text{control}}}$$

The compounds were tested on this model at concentrations of $5 \times 10^{-3}$ and $5 \times 10^{-4}$M.

c) Results

α) Activity of strontium 2-ethoxy-4-hydroxy-methyl-3-oxa pentanedioate obtained using ethyl β-D-glucopyrannoside as a starting material on osseous formation.

In vitro at a concentration of $10^{-4}$M, strontium 2-ethoxy-4-hydroxymethyl-3-oxa pentanedioate exercises a considerable and statistically significant stimulation of the osseous formation evaluated by incorporation of labeled proline (collagen synthesis).

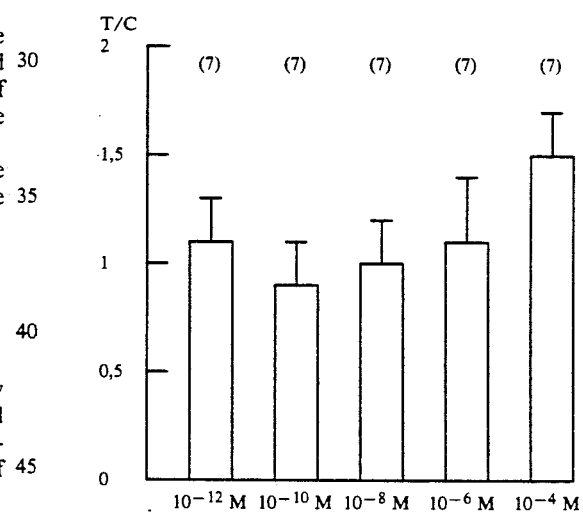

| | $10^{-12}$M | $10^{-10}$M | $10^{-8}$M | $10^{-6}$M | $10^{-4}$M |
|---|---|---|---|---|---|
| n | 7 | 7 | 7 | 7 | 7 |
| Mean | 1,0582 | 0.9717 | 1.0305 | 1.0740 | 1.4961** |
| ESD | 0.1381 | 0.0926 | 0.1139 | 0.2298 | 0.1905 |
| Maximum value | 1.2822 | 1.0974 | 1.2092 | 1.4652 | 1.8034 |
| Minimum value | 0.8988 | 0.8467 | 0.8511 | 0.8433 | 1.2095 |

β) Activity of strontium 2-ethoxy-4-hydroxy-methyl-3-oxa pentanedioate obtained using ethyl β-D-glucopyrannoside as the starting material on osseous resorption In vitro strontium 2-ethoxy-4-hydroxymethyl-3-oxa pentanedioate (A) exercises a considerable anti-resorbing activity which is statistically significant from a concentration of $5 \times 10^{-4}$M. This activity is dose-dependent. Despite the stimulation by PTH, at a concentration of $5 \times 10^{-3}$M (A) inhibits osseous resorption and brings it back to a level distinctly below the spontaneous resorption.

| | Level of osseous resorption (%) | | T/C | |
|---|---|---|---|---|
| | D1-D4 | D1-D7 | D1-D4 | D4-D7 |
| Absolute control | 6.8 ± 0.5 | 4.5 ± 1.9 | — | — |
| PTH | 14.3 ± 3.4 (a) | 37.0 ± 7.6 (b) | 1.00 | 1.00 |
| (A) 5 10$^{-4}$ | 14.5 ± 4.1 | 31.1 ± 8.34 (c) | 1.01 | 0.84 |
| (A) 5 10$^{-3}$ | 6.4 ± 0.9 (c) | 2.4 ± 0.5 (d) | 0.45 | 0.06 |

9 determinations per point
(a) - different from control at $p < 0.05$
(b) - different from control at $p < 0.0001$
(c) - different from PTH at $p < 0.05$
(d) - different from PTH at $p < 0.0001$

EXAMPLE 9 pharmacological study: bioavailability the determination was carried out on groups of 5 male wistar rats administration is in a dose of 50 mg of $Sr^{2+}$ per kg in the form of gelatin mini capsules, the determination was carried out by atomic absorption spectrometry using flame ionisation for the concentrations higher than 1 μg/ml and furnace ionisation for the concentrations lower than 1 μg/ml the absolute bioavailability of strontium 2-ethoxy-4-hydroxymethyl-3-oxa pentanedioate obtained using ethyl β-D-glucopyrannoside as the starting material is 60.5% compared with strontium chloride.

We claim:

1. An alkaline earth metal salt selected from those of the formula (I):

$$CR_1R_2\text{—}O\text{—}C(OR_4)(R_3)\text{—}OC(=O)\text{—}, (CHR_5)_i\text{—}CO_2^{\ominus}\ \ M^{2\oplus}$$ (I)

in which:

R$_1$, R$_2$, R$_3$ and R$_5$ each represent, independently of one another, a hydrogen atom, a straight-chain or branched lower alkyl group having 1 to 4 carbon atoms or a hydroxyl, hydroxyalkyl, alkoxy, alkoxyalkyl or carboxyalkyl group, i is 0 or 1, R$_4$ is a hydrogen atom, a straight-chain or branched lower alkyl group having 1 to 4 carbon atoms, an optionally substituted aryl or arylalkyl group or a carboxyalkyl group, with the proviso that when R$_1$=R$_3$=H, R$_2$=CH$_2$OH and i=0 and when R$_1$=R$_2$=R$_3$=H and i=0, R$_4$ is then other than CH$_3$, it being understood that the term substituted indicates that the aromatic ring of aryl or aralkyl may be substituted by one or more alkyl, nitro, alkoxy, hydroxyl, halogen, or trifluoromethyl groups, and M represents an alkaline earth metal, as well as their isomers, epimers, diastereoisomers and enantiomers, which may be isolated or in the form of a mixture.

2. The compound as claimed in claim 1 wherein the alkaline earth metal is strontium.

3. The compound as claimed in claim 1 wherein i=0, R$_1$=CH$_2$OH, R$_2$=R$_3$=H and R$_4$=straight-chain or branched lower alkyl having 2 to 4 carbon atoms or arylalkyl.

4. The compound as claimed in claim 1, which is strontium 2-ethoxy-4-hydroxymethyl-3-oxa pentanedioate and its SS, RR, SR and RS isomers, in the isolated form or in the form of a mixture having the formula $$HOCH_2\text{—}CH\text{—}O\text{—}CH(OCH_2CH_3)\text{—}CO^{\ominus}\text{—}OC\text{—}O\ Sr^{\oplus\oplus}\ O$$

5. The compound as claimed in claim 1, which is strontium 2-propoxy-4-hydroxymethyl-3-oxa pentanedioate and its SS, RR, SR and RS isomers, in the isolated form or in the form of the mixture having the formula $$HOCH_2\text{—}CH\text{—}O\text{—}CH(OCH_2CH_2CH_3)\text{—}CO^{\ominus}\text{—}OC\text{—}O\ Sr^{\oplus\oplus}\ O$$

6. A pharmaceutical composition useful for treatment of osseous conditions containing, as active principle, an effective amount of alkaline earth metal salt as claimed in claim 1 in combination with one or more pharmaceutically acceptable excipients or vehicles.

7. The composition as claimed in claim 6, containing strontium 2-ethoxy-4-hydroxymethyl-3-oxa pentanedioate as active principle.

8. A method for treating a living animal body afflicted with an osseous disease requiring stimulation of osseous formation comprising the step of administering to the said living animal an amount of a compound of claim 1 which is effective for alleviation of the said condition.

* * * * *

UNITED STATES PATENT AND TRADEMARK OFFICE
CERTIFICATE OF CORRECTION

PATENT NO. : 5,075,336

DATED : Dec. 24, 1991

INVENTOR(S) : Stanislas Czernecki, Claude Fugier, Yannis Tsouderos

It is certified that error appears in the above-identified patent and that said Letters Patent is hereby corrected as shown below:

Column 2, line 23; "(II):" should read -- (III): --.
Column 5, approximately line 42; (DCl$_3$, TMS)" should read -- (CDCl$_3$, TMS) --.
Column 6, approximately line 23; "CH$_3$;" should read --CH$_3$ 1; --.
Column 6, approximately line 55; "CH$_2$;" should read -- CH$_2$ 6; --.
Column 12, lines 44/45; "pharmaceutically acceptable" should read -- pharmaceutically-acceptable --. (PA 2-15-91, Pg. 2)

Signed and Sealed this

Thirteenth Day of April, 1993

*Attest:*

STEPHEN G. KUNIN

*Attesting Officer*     *Acting Commissioner of Patents and Trademarks*